United States Patent [19]

Brehier

[11] Patent Number: 5,000,179

[45] Date of Patent: Mar. 19, 1991

[54] CARDIAC STIMULATOR AND PROCESS FOR REGULATING THIS STIMULATOR

[75] Inventor: Jacques Brehier, Le Mans, France

[73] Assignee: Biovallees (French Societe Anonyme), France

[21] Appl. No.: 280,510

[22] Filed: Dec. 6, 1988

[30] Foreign Application Priority Data

Dec. 7, 1987 [FR] France .................. 87 16992

[51] Int. Cl.$^5$ ............................................. A61N 1/05
[52] U.S. Cl. .................................................. 128/419 P
[58] Field of Search ...... 128/419 P, 419 PG, 419 PT, 128/419 R

[56] References Cited

U.S. PATENT DOCUMENTS

| | | | |
|---|---|---|---|
| 4,245,643 | 1/1981 | Benzing, III et al. | 128/419 PT |
| 4,436,092 | 3/1984 | Cook et al. | 128/419 PG |
| 4,479,489 | 10/1984 | Tucci | 128/419 P |
| 4,545,380 | 10/1985 | Schroeppel | 128/419 P |
| 4,688,573 | 8/1987 | Alt | 128/419 PG |
| 4,694,830 | 9/1987 | Lekholm | 128/419 PG |
| 4,726,383 | 2/1988 | Cook et al. | 128/419 P |
| 4,766,902 | 8/1988 | Schroeppel | 128/419 P |
| 4,774,951 | 10/1988 | Osypka | 128/419 P |
| 4,803,987 | 2/1989 | Calfee et al. | 128/419 PG |
| 4,805,621 | 2/1989 | Heinze et al. | 128/734 |
| 4,870,967 | 10/1989 | Heinze et al. | 128/419 PG |

FOREIGN PATENT DOCUMENTS

| | | |
|---|---|---|
| 833040 | 6/1943 | France . |
| 1342670 | 9/1963 | France . |
| 1379694 | 10/1964 | France . |
| WO85/05279 | 12/1985 | World Int. Prop. O. . |

Primary Examiner—Lee S. Cohen
Assistant Examiner—Kennedy J. Schaetzle
Attorney, Agent, or Firm—Mason, Fenwick & Lawrence

[57] ABSTRACT

A cardiac stimulator is provided which is controlled by the arterial temperature of a patient. The cardiac stimulator includes a stimulation element connected to an electrical cell, and a connector connected to the stimulation element. A probe has a temperature sensor and at least one stimulation contact which are connected electrically to the connector by conductors. An adjustable electrical resistor, adjustable from outside the housing, is connected to the housing and is inserted in series between at least one of the conductors of the probe and the stimulation element. The cardiac stimulator also includes means for adjusting the adjustable electrical resistor which is accessible from outside the housing. This means for adjusting advantageously enables the setting of substantially the entire electrical resistance of the stimulation element after fitting, regardless of the arterial temperature and inherent resistance of the probe.

6 Claims, 1 Drawing Sheet

CARDIAC STIMULATOR AND PROCESS FOR REGULATING THIS STIMULATOR

FIELD OF THE INVENTION

The invention relates to an implantable cardiac stimulator and to a process for setting this stimulator.

PRIOR ART

More specifically, the invention relates to a cardiac stimulator of the type known per se, controlled by the arterial temperature of the patent equipped with this stimulator, the stimulator comprising, in the first place, a housing containing an electrical cell, stimulation means associated with the cell and a connector associated with the stimulation means and, in the second place, a probe intended to be associated with the connector by means of a first end part and, in its second end part, possessing on the one hand a temperature sensor, and on the other hand at least one stimulation contact which are connected electrically to the connector by means of conductors (the documents EP 0096464 and WO 85 05279).

Cardiac stimulators of this type have two problems: the first is to produce the temperature sensor so as to meet the requirements of accuracy, ease of assembly and fitting, cost, reliability and sealing which are demanded for this type of sensor. The second is the setting of the stimulator. In fact, the temperature sensor has a thermistor, the resistance of which varies as a function of the temperature. Now this resistance can be of the same order of magnitude as the resistance of the conductors of the probe or, at the very least, the resistances of the conductors of the probe are substantial and appreciable in relation to the resistance of the thermistor of the temperature sensor. If it is intended to use commercial probes in which, all things otherwise being equal, the variation in resistance is appreciable in relation to the sensitivity of the thermistor, it becomes necessary to carry out a setting of the cardiac stimulator. An electronic setting system is already known, but the disadvantage of this is that it consumes current, the aim being to avoid this where an implanted cardiac stimulator is concerned. Another possibility is to use probes of calibrated resistance, but the disadvantage of this solution is not only that it limits the use of various probes, but also that it does not solve the problem completely since the resistance can vary simply as a result of the actual assembly of the cardiac stimulator, particularly because of the connection between the probe itself and the connector of the housing, but also because the resistance of the probe with the temperature sensor depends on the arterial temperature of the patient, and this requires an initial setting of the basic value of the characteristic parameter of the cardiac stimulator, such as the stimulation frequency. The document WO 85 05279 provides a half-bridge for calibrating the thermistor at a reference temperature, but does not deal with the resistance of the stimulator/probe assembly, once it has been implanted.

A cardiac stimulator of a different type is also known (the document FR 1,379,694), and this possesses means of adjusting the frequency by means of needle screws changing an electrical resistance. However, because this setting is permanent, it is not intended to allow the use of a stimulator controlled by the arterial temperature of the patient.

SUMMARY OF THE INVENTION

The object of the invention is to overcome these disadvantages, and to achieve this it provides a stimulator of the above-mentioned type which comprises, associated with the housing and inserted in series between at least one of the conductors of the probe and the stimulation means, an electrical resistor which is adjustable from outside the housing and the function of which is to make it possible to set the electrical resistance of the stimulator together with its probe after fitting, whatever the arterial temperature and the inherent resistance of the probe.

According to another characteristic of the invention, the temperature sensor comprises a platinum wire which is seated in a sealed glass bulb and the two end parts of which emerge, the said bulb being seated sealingly in a housing made of an electrically conductive material neutral to blood, one of the end parts of the platinum wire being fastened mechanically and in electrical contact with the housing and the other end part passing sealingly through the housing.

The advantage of the invention is that the temperature sensor is produced in an especially simple, effective and reliable way, allowing easy assembly. Moreover, the "zero" setting of the stimulator after the implantation and fitting of the probe, especially its stimulation end, is easy because it is sufficient to actuate a movable setting member associated with the adjustable electrical resistor. In particular, this structure does not consume electrical energy.

BRIEF DESCRIPTION OF THE DRAWINGS

The other characteristics of the invention will emerge from the following description with reference to the accompanying drawings in which.

DESCRIPTION OF THE PREFERRED EMBODIMENT

Figure 1:
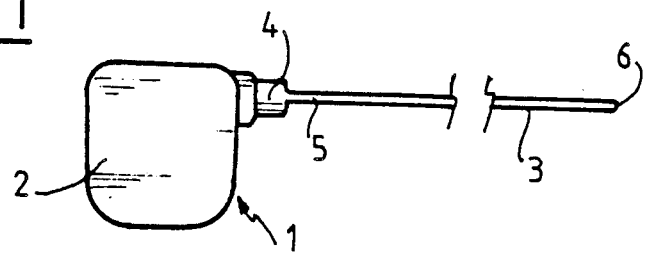
FIG. 1 is a general diagrammatic view of a cardiac stimulator according to the invention.
Figure 2:
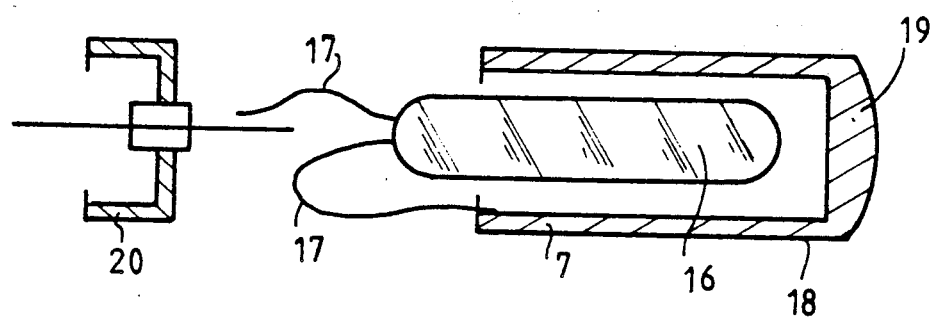
FIG. 2 is a diagrammatic view on a larger scale of the temperature sensor of the cardiac stimulator shown dismantled.
Figure 3:
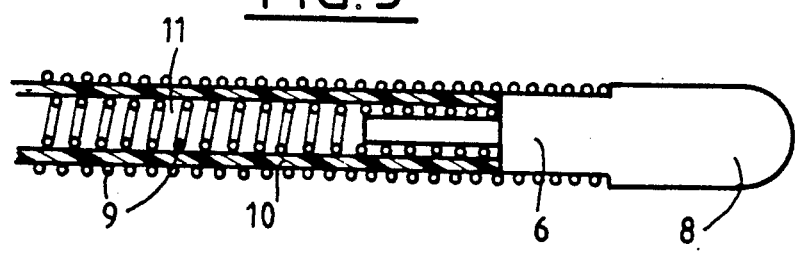
FIG. 3 is a partial diagrammatic view showing the stimulation and temperature-measuring end.
Figure 4:
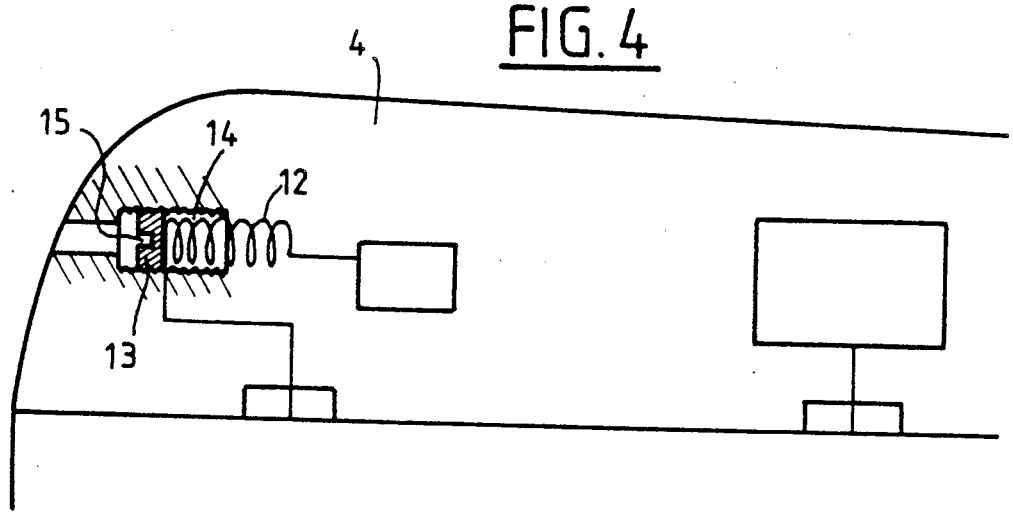
FIG. 4 is a partial diagrammatic view on a larger scale of the connector of the cardiac stimulator.

The invention relates to a cardiac stimulator 1 of the type controlled by the arterial temperature of the patient equipped with this stimulator. The stimulator comprises a housing 2 and a probe 3. The housing 2 contains, in a way known per se, an electrical cell, stimulation means (not shown) associated with the cell and a connector 4 associated mechanically with the housing 2 and electrically with the stimulation means.

The probe 3 is intended to be associated with the connector 4 in a first end part 5 and, in its second end part 6, possesses on the one hand a temperature sensor 7 and on the other hand at least one stimulation contact 8 which are connected electrically to the connector 4 by means of conductors 9. In a way likewise known per se, the probe 3 has two spirally wound and coaxial conductors 9 insulated by means of a sheath 10 made of a material, such as silicon, polyethylene, polyurethane or any other electrically insulating and biocompatible material. A central duct 11 is made in the probe 3 to allow the seating and sliding of a stiffener for fitting the probe at the moment of implantation.

According to the invention, the stimulator 1 possesses, associated with the housing 2 and inserted in series between at least one of the conductors 9 of the probe 3 and the stimulation means, an electrical resistor 12 which is adjustable from outside the housing 2 and the function of which is to make it possible to set the electrical resistance of the stimulator 1 together with its probe 3 after implantation, whatever the arterial temperature and the inherent resistance of the probe.

Consequently, the cardiac stimulator 1 according to the invention allows the use of probes 3 which can have different inherent characteristics, particularly electrical resistances, without thereby making the setting necessary for the smooth functioning of the stimulator either complex or so as to involve the consumption of electrical energy.

The electrical resistor 12 is place in the connector 4 and has a movable setting member 13 accessible from outside via a hole 14 made in the connector 4 and capable of being closed off sealingly and in a tamper-proof manner by means of an attached plug made of silicon or any other equivalent material (not shown).

The movable setting member 13 comprises, for example, a screw mounted in the thread of the hole 14, the screw interacting electrically with the resistor 12 so as to shunt part of this resistor, in such a way that the effective resistance interposed between the corresponding conductor 9 and the stimulation means is adjustable and depends on the position of the movable member 13. To make the setting easier, the movable member 13 preferably possesses a head having recessed or projecting reliefs 15, such as those capable of interacting with a screwdriver known per se.

The temperature sensor 7 comprises a platinum wire which is seated in a sealed glass bulb 16 and the two end parts 17 of which emerge. The glass bulb 16 is seated sealingly in a housing 18 made of an electrically conductive material neutral to blood. One of the end parts 17 is fastened mechanically and in electrical contact with the housing 18. The other end part 17 passes sealingly through the housing 18.

The housing 18 is preferably produced in two parts, namely a bottom 19 and a cover 20, and the end part 17 passing through the housing is preferably arranged so as to pass through the cover 20.

The housing 18 is preferably made of titanium or platinum, the cover 20 being fastened mechanically and sealingly to the bottom 19 by welding.

The temperature sensor 7 has a general cylindrical shape and is thus designed so that it can conveniently be associated with the end of the probe 3, particularly by screwing.

The invention also relates to a process for setting a cardiac stimulator of the above-described type, in which the folliwing operating phases are carried out:

The cardiac stimulator 1, that is to say the housing 2 and the probe 3, is implanted in the patient.

The cardiac stimulator 1 is set to its range of highest sensitivity, especially by remote control, this being carried out in a way known per se.

Action is then taken on the adjustable resistor 12, particularly by means of the member 13, in order to set the resistance of the stimulator 1 together with its probe 3 and therefore an externally measurable parameter characteristic and representative of the functioning of the cardiac stimulator 1, especially the stimulation frequency, this being carried out in order to obtain the desired value.

When this adjustment has been made, the hole 14 is closed off. The movable member 13 is designed to move only when it is subjected positively to a sufficient external force. Consequently, when the setting is completed and when the hole 14 has been closed off, the setting member 13 is rendered immobile and there can be no inopportune loss of setting, for whatever reason. For this purpose, the setting member 13, when it is in the form of a screw, can be mounted frictionally in the internally threaded hole 14.

I claim:

1. A cardiac stimulator controlled by arterial temperature of a patient, comprising:

a housing containing an electrical cell;

a stimulation means connected to the electrical cell;

a connector connected to the stimulation means;

a probe comprising first and second ends, for connection to the connector at the probe's first end, the probe's second end possessing a temperature sensor and at least one stimulation contact which are connected electrically to the connector by conductors;

an adjustable electrical resistor, adjustable from outside the housing, connected to the housing and inserted in series between at least one of the conductors of the probe and the stimulation means; and means for adjusting the adjustable electrical resistor, accessible from outside the housing, the means for adjusting enabling the setting of substantially the entire electrical resistance of the stimulation means after fitting, regardless of the arterial temperature and inherent resistance of the probe.

2. The cardiac stimulator of claim 1, further comprising a removable plug, and wherein the adjustable electrical resistor is disposed in the connector and possesses a movable setting member which is accessible from outside the connector via a hole in the connector and sealed off in a tamper-proof manner by the removable plug.

3. A cardiac stimulator controlled by arterial temperature of a patient, comprising:

a housing containing an electrical cell;

a stimulation means connected to the electrical cell;

a connector connected to the stimulation means;

a probe comprising first and second ends, for connection to the connector at the probe's first end, the probe's second end possessing a temperature sensor and at last one stimulation contact which are connected electrically to the connector by conductors;

wherein the temperature sensor comprises a platinum wire seated in a sealed glass bulb from which two ends of platinum wire extend, the bulb sealed in a temperature sensor housing comprising an electrically conductive material neutral to blood, one of the ends of the platinum wire being fastened mechanically and in electrical contact with the temperature sensor housing and the other end of the ends of the platinum wire passing in a sealed manner through the temperature sensor housing;

an adjustable electrical resistor, adjustable from outside the housing, connected to the housing and inserted in series between at least one of the conductors of the probe and the stimulation means; and means for adjusting the adjustable electrical resistor, accessible from outside the housing, the means for adjusting enabling the setting of the electrical resistance of the stimulation means after fitting, regardless of the arterial temperature and inherent resistance of the probe.

4. The cardiac stimulator of claim 3, wherein the temperature sensor housing comprises a bottom and a cover, the other of the ends of the platinum wire passing through the cover.

5. A process for setting a cardiac stimulator of any of claims 1, 2, 3, or 4, the method comprising the steps of:
   implanting the housing and the probe in the patient;
   setting the cardiac stimulator to its range of highest sensitivity;
   adjusting the adjustable resistor to set the resistance of the cardiac stimulator and its probe, and therefore setting an externally measurable representative and characteristic parameter such as stimulation frequency, so as to obtain a desired resistance and stimulation frequency; and
   closing off an access hole to the resistor.

6. The process of claim 5, wherein the step of setting the cardiac stimulator to its range of highest sensitivity comprises setting the cardiac stimulator to its range of highest sensitivity by remote control.

* * * * *